US012691191B2

(12) United States Patent
Duffner et al.

(10) Patent No.: US 12,691,191 B2
(45) Date of Patent: Jul. 28, 2026

(54) MEDICAL TUBE

(71) Applicant: Puray GmbH, Munich (DE)

(72) Inventors: Martin Duffner, Munich (DE);
Christina Weber, Munich (DE); Daniel Scherzer, Unterschleißheim (DE);
Erick Daniel Pano Paniagua, Munich (DE)

(73) Assignee: Puray GmbH, Munich (DE)

( * ) Notice: Subject to any disclaimer, the term of this patent is extended or adjusted under 35 U.S.C. 154(b) by 483 days.

(21) Appl. No.: 18/034,806

(22) PCT Filed: Oct. 28, 2021

(86) PCT No.: PCT/EP2021/080043
§ 371 (c)(1),
(2) Date: May 1, 2023

(87) PCT Pub. No.: WO2022/096370
PCT Pub. Date: May 12, 2022

(65) Prior Publication Data
US 2023/0398245 A1 Dec. 14, 2023

(30) Foreign Application Priority Data
Nov. 3, 2020 (EP) .................................... 20205545

(51) Int. Cl.
*A61L 2/10* (2026.01)
*A61L 2/26* (2006.01)
(Continued)

(52) U.S. Cl.
CPC *A61L 2/10* (2013.01); *A61L 2/26* (2013.01);
*A61N 5/0603* (2013.01);
(Continued)

(58) Field of Classification Search
None
See application file for complete search history.

(56) References Cited

U.S. PATENT DOCUMENTS 5,373,571 A * 12/1994 Reid ...................... A61B 18/22
385/128
5,695,482 A 12/1997 Kaldany
(Continued)

FOREIGN PATENT DOCUMENTS

| | | |
|---|---|---|
| EP | 1527798 A2 | 5/2005 |
| EP | 2744522 A1 | 6/2014 |
| WO | 2002102421 | 12/2002 |

OTHER PUBLICATIONS

"Raschotta, R., Silica Fibers, 2006, RP Photonics" (Year: 2006).*
(Continued)

*Primary Examiner* — Michael T. Holtzclaw
(74) *Attorney, Agent, or Firm* — ALG Intellectual Property, LLC

(57) ABSTRACT

Disclosed is a tube comprising at least one lumen, and a wall comprising at least one or a plurality of wave-guide(s). The wall encloses the at least one lumen. The tube comprises a distal end configured for being introduced into a body of a mammal and a proximal end comprising a tube-connector. The wave-guide(s) are configured to conduct electro-magnetic radiation along the tube. The tube is configured to emit at least a part of the radiation into the lumen and/or to an outer surface of the tube. The wave-guide(s) are configured for transmitting and side-emitting UV-light comprising a wave-length of 200-280 nm, preferably 210-260 nm, and still more preferably 210-230 nm. The wall comprises fluorinated ethylene-propylene. Further disclosed is a system comprising the tube and a radiation source configured for emitting electro-magnetic radiation, preferably UV-C (Continued)

light. Also, a method for using the tube is disclosed. The method comprises applying the tube to a body of a patient.

19 Claims, 5 Drawing Sheets

(51) Int. Cl.
*A61L 103/15* (2026.01)
*A61N 5/06* (2006.01)

(52) U.S. Cl.
CPC ........ *A61N 5/0624* (2013.01); *A61L 2103/15* (2026.01); *A61L 2202/11* (2013.01); *A61N 2005/061* (2013.01); *A61N 2005/063* (2013.01); *A61N 2005/0661* (2013.01)

(56) References Cited

U.S. PATENT DOCUMENTS

| | | | | |
|---|---|---|---|---|
| 10,279,058 | B2 | 5/2019 | Lin et al. | |
| 11,241,585 | B2 | 2/2022 | Long et al. | |
| 2004/0093044 | A1* | 5/2004 | Rychnovsky | A61N 5/062 |
| | | | | 607/93 |
| 2005/0171520 | A1* | 8/2005 | Farr | A61B 18/245 |
| | | | | 606/15 |
| 2013/0060188 | A1 | 3/2013 | Bedwell et al. | |
| 2018/0289940 | A1 | 10/2018 | Spotnitz et al. | |
| 2019/0168023 | A1 | 6/2019 | Eltorai | |
| 2019/0192814 | A1 | 6/2019 | Tang et al. | |
| 2020/0276342 | A1 | 9/2020 | Zaborsky | |
| 2021/0244840 | A1* | 8/2021 | Mermel | A61L 2/10 |
| 2022/0323787 | A1 | 10/2022 | Eltorai et al. | |
| 2022/0387643 | A1* | 12/2022 | Baarman | A61L 2/10 |

OTHER PUBLICATIONS

"International Search Report for Application No. PCT/EP2021/080043, mailed on Jan. 26, 2022".

Buonanno, et al., "207-nm UV Light—A Promising Tool for Safe Low-Cost Reduction of Surgical Site Infections. II: In-Vivo Safety Studies", PLoS ONE 11(6):e0138418. doi:10.1371/journal.pone. 0138418 (Jun. 8, 2016).

Buonanno, et al., "Germicidal Efficacy and Mammalian Skin Safety of 222-nm UV Light", Radiation Research 187, 493-501 (2017).

Narita, et al., "Disinfection and healing effects of 222-nm UVC light on methicillin-resistant *Staphylococcus aureus* infection in mouse wounds", Journal of Photochemistry and Photobiology B: Biology, vol. 178, Jan. 2018, pp. 10-18.

Welch, et al., "Far-UVC light: A new tool to control the spread of airborne-mediated microbial diseases.", Scientific Reports, 2018, 8:2752, doi:10.1038/s41598-018-21058.

Welch, et al., "Measurement of UV emission from a diffusing optical fiber using radiochromic film", Photochemistry and Photobiology, vol. 93, Issue 6, Jun. 2, 2017 https://doi.org/10.1111/php. 12798.

* cited by examiner

Prior Art

10

20

30

A-A

MEDICAL TUBE

The present invention relates to the field of medical instruments and devices. More particularly, the present invention relates to the field of catheters and sterile devices.

Catheters are long-known for use in treatment of patients, e.g. as urinary catheters. However, using catheters also results in increased risk for the patients' health due to nosocomial infections.

Buonanno M, Stanislauskas M, Ponnaiya B, Bigelow A W, Randers-Pehrson G, et al. (2016): "207-*nm UV Light—A Promising Tool for Safe Low-Cost Reduction of Surgical Site Infections. II: In-Vivo Safety Studies*.", PLOS ONE 11(6): e0138418. https://doi.org/10.1371/journal.pone.0138418 aims at testing the biophysically-based hypothesis that 207 nm UV light is not cytotoxic to exposed mammalian skin in vivo. They conclude that 207-nm light does not appear to be significantly cytotoxic to mouse skin and that these results suggest that excimer-based far-UVC light could potentially be used for its anti-microbial properties, but without the associated hazards to skin of conventional germicidal UV lamps.

Welch, D., Buonanno, M., Grilj, V. et al. Far-UVC light (2018): "A new tool to control the spread of airborne-mediated microbial diseases.", in *Sci Rep* 8, 2752. https://doi.org/10.1038/s41598-018-21058-w discusses the use of far-UVC light for inactivating bacteria without harm to exposed mammalian skin.

Buonanno, M., Ponnaiya, B., Welch, D., Stanislauskas, M., Randers-Pehrson, G., Smilenov, L., Lowy, F. D., Owens, D. M., & Brenner, D. J. (2017): "*Germicidal Efficacy and Mammalian Skin Safety of 222-nm UV Light*", Radiation research, 187(4), 483-491. https://doi.org/10.1667/RR0010CC.1 investigates effects of 222 nm light on human skin by means of in vivo and in vitro studies.

Kouji Narita, Krisana Asano, Yukihiro Morimoto, Tatsu-shi Igarashi, Michael R. Hamblin, Tianhong Dai, Akio Nakane (2018): "*Disinfection and healing effects of 222-nm UVC light on methicillin-resistant Staphylococcus aureus infection in mouse wounds*", Journal of Photochemistry and Photobiology B: Biology, 178, 10-18, https://doi.org/10.1016/j.jphotobiol.2017.10.030; Narita, K., Asano, K., Morimoto, Y., Igarashi, T., & Nakane, A. (2018): "Chronic irradiation with 222-nm UVC light induces neither DNA damage nor epidermal lesions in mouse skin, even at high doses", PloS one, 13(7), e0201259, https://doi.org/10.1371/journal.pone.0201259; and Yamano, N., Kunisada, M., Kaidzu, S., Sugihara, K., Nishiaki-Sawada, A., Ohashi, H., Yoshioka, A., Igarashi, T., Ohira, A., Tanito, M. and Nishigori, C. (2020): "*Long-term Effects of 222-nm ultraviolet radiation C Sterilizing Lamps on Mice Susceptible to Ultraviolet Radiation*", Photochem Photobiol, 96: 853-862, investigate and discuss effects of 222 nm UVC-radiation on skin of mice.

Welch, D., Spotnitz, H. M., & Brenner, D. 3. (2017): "*Measurement of UV emission from a diffusing optical fiber using radiochromic film*", Photochemistry and Photobiology, 93(6), 1509-1512 discusses optical fibres as well as an approach for measuring their UV-emissions.

WO 2002/102421 A1 teaches methods and apparatus for sterilizing or disinfecting using ultraviolet light. One embodiment of the invention is directed to a method for sterilizing or disinfecting at least a portion of an interior surface of a catheter, the interior surface being defined by a wall (24). The method comprises acts of identifying a stagnation zone (17) in the catheter, and transmitting ultraviolet light through the wall (24) at the stagnation zone (17).

Another embodiment of the invention is directed to an ultraviolet light-transmissive catheter. The catheter comprises a wall (24) defining an interior of the catheter, and a region (19) of the wall (24) adapted to transmit ultraviolet light.

U.S. Pat. No. 10,279,058 B2 discloses systems, methods, and kits for sterilizing in vivo catheters using an optical fiber to deliver UV light. In an embodiment, a method for sterilizing a catheter with at least a first lumen, includes inserting a distal end of a fiber optic cable into a fiber insertion port of a catheter connector attached to a hub of the first lumen, flushing the first lumen with fluid from a fluid source, inserting the fiber optic cable into the first lumen until a stopper of the fiber optic cable is adjacent to the fiber insertion port, providing light to the fiber optic cable from a light source after the fiber optic cable is inserted into the first lumen, withdrawing the fiber optic cable from the first lumen while the light is provided, and ceasing to provide light to the fiber optic cable after the fiber optic cable is withdrawn from the first lumen. The disclosure is also applicable to catheters with multiple lumens and to catheters accessed through subcutaneous ports.

The above citations are incorporated by reference in their entirety.

It is an object of the present invention to provide an improved tube, system and method for medical use.

It is further an optional object of the present invention to provide a tube, system and method for using thereof with improved disinfection properties.

In a first embodiment, a tube is comprised. The tube comprises at least one lumen, and a wall comprising at least one or a plurality of wave-guide(s). The wave-guide(s) are configured to conduct electro-magnetic radiation along the tube. The tube is configured to emit at least a part of the radiation into the lumen and/or to an outer surface of the tube.

Wherever reference is made in the following to the "wave-guide(s)", the at least one or the plurality of wave-guides are meant. For the sake of clarity, verbs are used in the plural form, but may also refer to the singular form of the at least one wave-guide.

The tube may be a medical tube. The tube may be a catheter. The tube may comprise a diameter of not more than 20 mm, preferably not more than 15 mm and still more preferably not more than 12 mm.

The wave-guide(s) may be elements configured for at least partially conducting electro-magnetic radiation. For example, the wave-guide(s) may be optic fibers.

The at least one lumen may be a hollow part of the tube. The tube may comprise a plurality of hollow parts that may each link a first end of the tube and a second end of the tube.

The wall may enclose the at least one lumen.

The at least one lumen may be a plurality of lumens. In such embodiments, the wall may enclose the lumens and further each of the lumens. For example, the wall may comprise separators separating the lumens from each other.

However, in embodiments with the plurality of lumens, the wall may also comprise a plurality of inner tubes, each inner tube enclosing one lumen. The inner tubes may in this case comprise same materials or consist of same materials as the wall.

The wave-guide(s) and the lumen may be substantially parallel to each other.

The lumen may comprise at least a portion of the wave-guide(s). For example, a portion of a surface of the wave-guide(s) may be a common surface with the lumen.

The wall of the tube may be the wave-guide(s), e.g. in a case of a material configured for transmitting the electro-magnetic radiation.

At least one of the wave-guide(s) may be located within the lumen at least along a portion of the tube. For example, said at least one of the wave-guide(s) may be located within the lumen and attached to the wall of the tube.

The wave-guide(s) may be side-emitting. In other words, the wave guides may be configured for laterally emitting at least a portion of the electro-magnetic radiation. This may optionally advantageously allow for transmission of the electro-magnetic radiation into the lumen and/or to an outer surface of the tube over at least a portion of a length of the tube. Hence, optionally, a disinfection of the outer surface and/or the lumen by means of the electro-magnetic radiation may be rendered possible.

The wave-guide(s) may be configured for side-emitting at least a portion of the electro-magnetic radiation into the wall.

The wall may be configured for transmitting at least a portion of the electro-magnetic radiation emitted by the wave-guide(s) to the outer surface of the tube.

The outer surface of the tube may be at least partially transparent to the electro-magnetic radiation.

The wall may be configured for transmitting at least a portion of the electro-magnetic radiation emitted by the wave-guide(s) to at least one of the at least one lumen. In other words, the wall may be configured for transmitting at least a portion of the radiation to one of the lumen(s). This may be optionally advantageous in cases where there are several lumens and at least one thereof does not need to be sterilized, e.g. a lumen for air or a medium to fill a balloon for keeping the tube in place.

The wall may be configured for transmitting at least a portion of the electro-magnetic radiation emitted by the wave-guide(s) to the at least one lumen. In other words, the wall may be configured transmitting at least a portion of the radiation to each of the lumens. This may be optionally advantageous for disinfection of all lumens.

The tube may comprise a distal end configured for being introduced into a body of a mammal. The distal end may for example comprise an adapted shape for improved insertion.

The tube may further comprise a proximal end. The proximal end may be an end opposite to the distal end of the tube. The proximal end may comprise a connector, such as a tube connector, which will be discussed later on.

In embodiments wherein the wave-guide(s) are the plurality of wave-guides, each of the plurality of wave-guides may be spaced from each other over at least 50%, preferably at least 75% and still more preferably at least 90% of their length within a portion of the wall that is configured to be introduced into the body of the mammal. This may be optionally advantageous for an improved and more even distribution of the electro-magnetic radiation.

The plurality of the wave-guides may be guided helically along a length of the tube.

The plurality of wave-guides may be arranged substantially parallel to each other.

The plurality of wave-guides may be arranged as a chain. In other words, the tube may comprise multiple wave-guides, wherein the wave-guides are connected to a successor and predecessor, apart from the first and the last wave-guide, which are each only connected to one of the other wave-guide(s).

The plurality of wave-guides may be substantially mechanically held together.

The plurality of wave-guides may enter a substantially formfitting connection.

The plurality of wave-guides may enter a substantially non-positive connection.

The plurality of wave-guides may enter a substantially substance-to-substance bonding.

The wave-guide(s) may be enclosed by the wall.

The wave-guide(s) may be non-detachable. In other words, the wave-guide(s) may not configured to be detachable from the tube by a user. However, they may be detachable with appropriate tools or processes, e.g. for the purpose of recycling and/or waste treatment.

The wave-guide(s) may be permanently attached to at least a portion of the wall. In other words, the wave-guide(s) may be immobile with respect to at least the portion of the wall.

The wave-guide(s) may be flexible. This may be optionally advantageous for easier introduction of the tube into the body of the mammal.

The wave-guide(s) may be configured for transmitting and side-emitting UV-light comprising a wave-length of 200-280 nm, preferably 210-260 nm, and still more preferably 210-230 nm. This may be optionally advantageous, as light in these intervals may inactivate bacteria and at least some viruses.

The wave-guide(s) may be configured for transmitting and side-emitting UV-light comprising a wave-length of 222 nm. This may be optionally advantageous, as UV light comprising said wave-length may not be harmful for mammalian skin, as pointed out by Welch, Buonanno et al. (see above).

The wave-guides may be configured for transmitting and side-emitting visible light. In this disclosure, electro-magnetic radiation comprising a wavelength between 400 nm and 700 nm is considered visible light. Transmission and side-emitting features for visible light may be optionally advantageous as visible light can be perceived by humans. Thus, safety and facilitated function-control may optionally be enabled.

The wave-guide(s) may comprise a gradient of a side-emittance of the UV-light. The side-emittance may be a portion of the light that is emitted laterally relative to light that entered a corresponding part of the wave-guide(s), e.g.

$$\frac{E_{emitted}}{l \cdot E_{received}},$$

wherein $E_{emitted}$ is an energy of electro-magnetic radiation emitted laterally in the part, l is a length of the part, and $E_{received}$ is an energy of electro-magnetic radiation received by the part.

The side-emittance of the UV-light may increase from the proximal to the distal end. This may be optionally advantageous for a more even radiation level along the tube.

Each of the wave-guide(s) may comprise an optic fibre.

The optic fibre may comprise a silica fibre.

The optic fibre may comprise a high-OH silica core.

The wave-guide(s) may be configured to be side-emitting by means of scattering centers.

The wave-guide(s) may be configured to be side-emitting by means of by a partially removed cladding. In other words, the cladding of the optic fibre may be at least partially removed.

The wave-guide(s) may comprise a liquid light guide. The liquid light guide may comprise a canal for a light guide liquid, which canal comprises the light guide liquid. An example for a liquid light guide is discussed in EP 0 963 565 B1.

The light guide liquid may comprise a refractive index above a refractive index of the canal. The refractive index may be the refractive index for UV-C light, particularly for light comprising a wave-length of 222 nm.

The inner surface of the canal of the wave-guide(s) may be configured for side-emitting a portion of the electro-magnetic radiation. For example, the inner surface of the canal may comprise imperfections, such as an increased surface roughness or ripples.

The wall may comprise a polymer, such as silicone, latex, low density polyethylene, high density polyethylene, poly-amide, polytetrafluoroethylene (PTFE), ethylene tetrafluo-roethylene (ETFE) or fluorinated ethylene propylene (FEP).

The wall may consist to at least 60%, preferably at least 70% and still more preferably at least 80% of the polymer. In other words, at least 60% of a mass of the wall may consist of the polymer, preferably at least 70%, and still more preferably at least 80% of the mass may consist of the polymer.

The polymer may be biocompatible.

The polymer may be a thermoplastic.

The tube may be flexible. For example, the bending radius may be below 10 cm, preferably below 5 cm. This may be optionally advantageous for introducing the tube into the body of the mammal. An optional advantage may result from the use of the liquid light guide, since the liquid light guide may comprise a lower bending radius than a solid wave-guide(s).

The polymer may be UV-transparent. In other words, the polymer may be configured for transmitting a substantial part of UV-radiation irradiating it. In this disclosure, the term "UV-transparent" is intended to also encompass mate-rials that transmit but disperse UV light, as long as said materials do not reflect or absorb a substantial part of UV-radiation by which they are irradiated.

The polymer may be transparent. In other words, the polymer may be transparent to visible light. In this disclo-sure, the term "transparent to visible light" is intended to also encompass materials that transmit but disperse visible light, as long as said materials do not reflect or absorb a substantial part of visible light by which they are irradiated.

The polymer may be a fluoropolymer, such as FEP, ETFE or PTFE. This may be optionally advantageous due to the chemical resistance of fluoropolymers as well as their UV-resistance.

The fluoropolymer may be fluorinated ethylene-propyl-ene, also known as FEP. This may be optionally advanta-geous due to its biocompatibility, flexibility, resistance to detergents, transparency to visible light and UV-transpar-ency. This may be optionally advantageous due to high UV-transparency of FEP.

The fluoropolymer may be ethylene tetrafluoroethylene (ETFE).

The wall may comprise a Young modulus in a range from 440 to 640 MPa.

The lumen may comprise a cross-section area.

The cross-section area of the lumen may comprise a negative gradient along the tube from the proximal to the distal end.

The wall of the tube may comprise a cross-section area. The cross-section area of the tube may comprise a negative gradient along the tube from the proximal to the distal end.

These options may be optionally advantageous, as they may allow for compensating for a decreasing intensity of the radiation along the catheter.

The tube may comprise a diffusor at the distal end.

The diffusor may be a spherical diffusor.

The diffusor may be configured for scattering the UV-light into a hollow organ of the body of the mammal, such as the bladder. For example, the diffusor may be configured for scattering the UV-light into the hollow organ when the tube is introduced into the body of the mammal.

The tube may comprise a fluorescent element.

The fluorescent element may be fluorescent under UV-light, preferably under UV-light comprising a wavelength of 210 nm-230 nm. This may be optionally advantageous, as it may provide a visual indicator for a presence of UV-light in the tube and may thus increase a fail-safety or a safety of the tube.

The fluorescent element may extend circumferentially around a portion of the tube. The fluorescent element may enclose at least 60%, preferably 80% and still more prefer-ably 90% of a circumference of the tube at a certain axial position. For example, the fluorescent element be ring-shaped.

The fluorescent element may be stripe-shaped.

The tube may be a catheter. For example, the tube may be at least one of a cardiovascular catheter, an urological catheter, a gastrointestinal catheter, a neurovascular catheter, an ophthalmic catheter, a dialysis catheter and a chest catheter. The tube may particularly be an urinary catheter.

The tube may be a drain.

The tube may be an infusion tube.

The lumen may be configured for guiding at least one of a medical tool and a medical sample.

The wave-guide(s) may be configured for transmitting radiation configured for spectroscopy analysis of the mam-mal.

The diffusor may be configured for scattering the light configured for the spectroscopy analysis, such as infrared light.

The tube comprises may comprise a sensor. The sensor may also be referred to as a sensing unit. The sensor/sensing unit may be configured to be connected to an analysis device.

The sensor may be located at or next to the distal end of the tube.

The sensor may comprise at least one of a camera, a temperature-sensing unit, a pH value-sensing unit, a pulse rate-sensing unit, a pressure-sensing unit, a blood sugar-sensing unit, and a sensing unit configured for blood gas-analysis.

The tube may comprise a tube-connector. The tube-connector may be an adaptor or connector configured for connecting to the tube to one, at least one or a plurality of connectors.

The tube-connector may be configured to connect the wave-guide(s) to a radiation source. The radiation source may be configured for generating the electro-magnetic radia-tion.

The tube-connector may comprise a socket.

The tube-connector may be configured for receiving an optic fibre cable from the radiation source.

The tube-connector may comprise a plug.

The plug may be configured to be inserted into a socket of a light source, The plug may be connected to the waveguide(s).

The tube-connector may be configured for connecting at least one of the at least one lumen with a drain for fluid, such as a collector bag.

The tube-connector may be configured for connecting at least one of the at least one lumen with a source of fluid. In other words, the tube-connector may comprise a fluid intake that is connected to at least one of the at least one lumen.

The tube may be configured for transmitting a read-out of the sensor to the connector.

In a second embodiment, a system is disclosed.

The system comprises the tube further the radiation source. The radiation source is configured for emitting electro-magnetic radiation.

The electro-magnetic radiation emitted by the radiation source may comprise UV-light. In other words, the radiation source may be configured for emitting electro-magnetic radiation comprising UV-light.

The UV-light may be UV-C light.

The electro-magnetic radiation emitted by the radiation source may comprise electro-magnetic radiation comprising a wavelength of 222 nm.

At least 50%, preferably at least 80%, still more preferably 90% and most preferably at least 95% of the electro-magnetic radiation may comprise a wavelength of 222+−5 nm. The percentage-indications may refer to a share of the radiation by power or energy per time unit.

A least 50%, preferably at least 80%, still more preferably 90% and most preferably at least 95% of the electro-magnetic radiation may comprise a wavelength of substantially 222 nm.

The radiation source may be configured for generating monochromatic light.

The system may be configured for releasing the electro-magnet radiation substantially evenly over a length of the tube. This may be optionally advantageous for ensuring a safe disinfection of the tube without unnecessarily high radiation doses at certain points or parts of the tube.

The system may be configured for releasing UV-light from the tube comprising a radiant energy density of 0.1 mJ/cm²-300 mJ/cm².

The system may be configured for releasing UV-light from the tube comprising a radiant energy density of 1 mJ/cm² to 100 mJ/cm².

The system may be configured for releasing UV-light from the tube comprising a radiant energy density of 10 mJ/cm²-20 mJ/cm².

The system may be configured for releasing UV-light from the tube comprising a radiant energy density of around 15 mJ/cm².

The system may, for example in case of continuous operation, be configured for releasing UV-light from the tube comprising a radiant power density of less than 0.05, preferably 0.01 mW/cm².

The system may be configured for intermittingly emitting the electro-magnetic radiation.

The system may be configured for intermittingly emitting the UV-C light. This may be optionally advantageous for safely disinfecting the tube and however not causing an excessive ageing of the tube or damages of the mammalian tissue.

The radiation source may comprise at least one of a UV-C light emitting diode, a laser and a filtered excimer lamp configured for generating the UV-C light.

The electro-magnetic radiation emitted by the radiation source may comprise visible light.

At least a portion of the wall of the tube may be configured for emitting the visible light.

The radiation source may comprise a component configured for generating the visible light, such as an LED.

The radiation source may comprise a source-connector configured to connect the radiation source to the tube-connector.

The source-connector may comprise a socket for receiving the plug of the tube-connector.

The radiation source may be configured to only provide radiation when the tube-connector and the source-connector are in a connected state. Providing the radiation may refer to providing the radiation to an outside of the radiation source. Not providing the radiation may thus for example be achieved by not powering the radiation source, but it may for example also be achieved by guiding the radiation into a beam trap inside the radiation source.

The system may comprise a safety switch configured for preventing the radiation source from providing radiation when the tube-connector and the source-connector are not in a connected state. The person skilled in the art will easily understand that the system may however comprise an option for bypassing this limitation, e.g. for testing or maintenance purpose. In other words, the system may comprise a safety switch configured for preventing the radiation source in normal operation from providing radiation when the tube-connector and the source-connector are not in a connected state.

The safety switch may for example be a button in the connection of the source-connector and the tube-connector, which is actuated by the connection. However, the safety switch may also be implemented differently, e.g. by means of an electric connection that is closed when the two connectors are connected, or still differently.

The source-connector may comprise a plug configured to be plugged into the socket of the tube-connector.

In a third embodiment, a method is disclosed.

The method is a method for using the above-disclosed tube. The method comprises applying the tube to the body of a patient.

The method may further comprise connecting the tube to a source of UV-light, such as the radiation source.

The method may comprise collecting a bodily fluid by means of the tube.

The method may comprise introducing a liquid into a human body by means of the tube.

The method may comprise introducing a surgical instrument into the human body by means of the tube.

Further, a method for using the above-disclosed system is disclosed. The method comprises applying the tube of the system to the body of the patient.

The method for using the system may further comprise connecting the tube to the radiation source.

The method for using the system may comprise collecting a bodily fluid by means of the tube of the system.

The method for using the system may comprise introducing a liquid into a human body by means of the tube of the system.

The method for using the system may comprise introducing the surgical instrument into the human body by means of the tube.

The method for using the system may further comprise connecting the system to the power source.

The following embodiments also form part of the invention.

Tube Embodiments

Below, embodiments of a tube will be discussed. The tube embodiments are abbreviated by the letter "T" followed by a number. Whenever reference is herein made to the "tube embodiments", these embodiments are meant.

T1. A tube comprising
at least one lumen, and
a wall comprising at least one or a plurality of wave-guide(s),
wherein the wave-guide(s) are configured to conduct electro-magnetic radiation along the tube and wherein the tube is configured to emit at least a part of the radiation into the lumen and/or to an outer surface of the tube.

T2. The tube according to the preceding embodiment, wherein the wall encloses the at least one lumen.

T3. The tube according to any of the preceding embodiments, wherein the at least one lumen is a plurality of lumens.

T4. The tube according to any of the preceding embodiments, wherein the wave-guide(s) and the lumen are substantially parallel to each other.

T5. The tube according to any of the preceding embodiments, wherein the lumen comprises at least a portion of the wave-guide(s).

T6. The tube according to any of the preceding embodiments, wherein the wall of the tube is the wave-guide(s).

T7. The tube according to any of the preceding embodiments, wherein at least one of the wave-guide(s) is located within the lumen at least along a portion of the tube.

T8. The tube according to any of the preceding embodiments, wherein the wave-guide(s) are side-emitting.

T9. The tube according to any of the preceding embodiments, wherein the wave-guide(s) are configured for side-emitting at least a portion of the electro-magnetic radiation into the wall.

T10. The tube according to any of the preceding embodiments with the features of T8, wherein the wall is configured for transmitting at least a portion of the electro-magnetic radiation emitted by the wave-guide(s) to the outer surface of the tube.

T11. The tube according to the preceding embodiment, wherein the outer surface of the tube is at least partially transparent to the electro-magnetic radiation.

T12. The tube according to any of the preceding embodiments with the features of T8, wherein the wall is configured for transmitting at least a portion of the electro-magnetic radiation emitted by the wave-guide(s) to at least one of the at least one lumen.

T13. The tube according to any of the preceding embodiments with the features of T8, wherein the wall is configured for transmitting at least a portion of the electro-magnetic radiation emitted by the wave-guide(s) to the at least one lumen.

T14. The tube according to any of the preceding embodiments, wherein the tube comprises a distal end configured for being introduced into a body of a mammal.

T15. The tube according to any of the preceding embodiments, wherein the tube comprises a proximal end comprising a connector.

T16. The tube according to any of the preceding embodiments, wherein each of the plurality of wave-guides are spaced from each other over at least 50%, preferably at least 75% and still more preferably at least 90% of their length within a portion of the wall that is configured to be introduced into the body of the mammal.

T17. The tube according to the preceding embodiment, wherein the plurality of wave-guides is guided helically along a length of the tube.

T18. The tube according to any of the preceding embodiments, wherein the plurality of wave-guides are arranged substantially parallel to each other.

T19. The tube according to any of the preceding embodiments but the preceding three, wherein the plurality of wave-guides is arranged as a chain.

T20. The tube according to any of the preceding embodiments, wherein the plurality of wave-guides is substantially mechanically held together.

T21. The tube according to any of the preceding embodiments, wherein the plurality of wave-guides enters a substantially formfitting connection.

T22. The tube according to any of the preceding embodiments, wherein the plurality of wave-guides enters a substantially non-positive connection.

T23. The tube according to any of the preceding embodiments, wherein the plurality of wave-guides enters a substantially substance-to-substance bonding.

T24. The tube according to any of the preceding embodiments, wherein the wave-guide(s) are enclosed by the wall.

T25. The tube according to any of the preceding embodiments, wherein the wave-guide(s) are non-detachable.

T26. The tube according to any of the preceding embodiments, wherein the wave-guide(s) are permanently attached to at least a portion of the wall.

T27. The tube according to any of the preceding embodiments, wherein the wave-guide(s) are flexible.

T28. The tube according to any of the preceding embodiments, wherein the wave-guide(s) are configured for transmitting and side-emitting UV-light comprising a wave-length of 200-280 nm, preferably 210-260 nm, and still more preferably 210-230 nm.

T29. The tube according to any of the preceding embodiments, wherein the wave-guide(s) are configured for transmitting and side-emitting UV-light comprising a wave-length of 222 nm.

T30. The tube according to any of the preceding embodiments, wherein the wave-guides are configured for transmitting and side-emitting visible light.

T31. The tube according to any of the preceding embodiments with the features of T8, wherein the wave-guide(s) comprise a gradient of a side-emittance of the UV-light.

T32. The tube according to the preceding embodiment, wherein the side-emittance of the UV-light increases from the proximal to the distal end.

T33. The tube according to any of the preceding embodiments, wherein each of the wave-guide(s) comprises an optic fibre.

T34. The tube according to the preceding embodiment, wherein the optic fibre comprises a silica fibre.

T35. The tube according to any of the two preceding embodiments, wherein the optic fibre comprises a high-OH silica core.

T36. The tube according to any of the preceding embodiments with the features of T8 and T33, wherein the wave-guide(s) are configured to be side-emitting by means of scattering centers.

T37. The tube according to any of the preceding embodiments with the features of T8 and T33, wherein the wave-guide(s) are configured to be side-emitting by means of by a partially removed cladding.

T38. The tube according to any of the preceding embodiments, wherein the wave-guide(s) comprise a liquid light guide, wherein the liquid light guide comprises a canal for a light guide liquid, which canal comprises the light guide liquid.

T39. The tube according to the preceding embodiment, wherein the light guide liquid comprises a refractive index above a refractive index of the canal.

T40. The tube according to any of the preceding embodiments with the features of T8 and T38, wherein the inner surface of the canal of the wave-guide(s) is configured for side-emitting a portion of the electromagnetic radiation.

T41. The tube according to any of the preceding embodiments, wherein the wall comprises a polymer.

T42. The tube according to the preceding embodiment, wherein the wall consists to at least 60%, preferably at least 70% and still more preferably at least 80% of the polymer.

T43. The tube according to any of the preceding embodiments with the features of T41, wherein the polymer is biocompatible.

T44. The tube according to any of the preceding embodiments with the features of T41, wherein the polymer is a thermoplastic.

T45. The tube according to any of the preceding embodiments with the features of T41, wherein the tube is flexible.

T46. The tube according to any of the preceding embodiments with the features of T41, wherein the polymer is UV-transparent.

T47. The tube according to any of the preceding embodiments with the features of T41, wherein the polymer is transparent.

T48. The tube according to any of the preceding embodiments with the features of T41, wherein the polymer is a fluoropolymer.

T49. The tube according to the preceding embodiment, wherein the fluoropolymer is fluorinated ethylene-propylene.

T50. The tube according to any of the preceding embodiments, wherein the wall comprises a Young modulus in a range from 440 to 640 MPa.

T51. The tube according to any of the preceding embodiments and with the features of T14, wherein the lumen comprises a cross-section area, wherein the cross-section area of the lumen comprises a negative gradient along the tube from the proximal to the distal end.

T52. The tube according to any of the preceding embodiments and with the features of T14, wherein the wall of the tube comprises a cross-section area, and wherein the cross-section area of the tube comprises a negative gradient along the tube from the proximal to the distal end.

T53. The tube according to any of the preceding embodiments with the features of T14, wherein the tube comprises a diffusor at the distal end.

T54. The tube according to the preceding embodiment, wherein the diffusor is a spherical diffusor.

T55. The tube according to any of the two preceding embodiments, wherein the diffusor is configured for scattering the UV-light into a hollow organ of the body of the mammal, such as the bladder.

T56. The tube according to any of the preceding embodiments, wherein the tube comprises a fluorescent element.

T57. The tube according to the preceding embodiment, wherein the fluorescent element is fluorescent under UV-light, preferably under UV-light comprising a wavelength of 210 nm-230 nm.

T58. The tube according to any of the two preceding embodiments, wherein the fluorescent element extends circumferentially around a portion of the tube.

T59. The tube according to any of the preceding embodiments with the features of T56, wherein the fluorescent element is stripe-shaped.

T60. The tube according to any of the preceding embodiments, wherein the tube is a catheter.

T61. The tube according to any of the preceding embodiments, wherein the tube is a drain.

T62. The tube according to any of the preceding embodiments, wherein the tube is an infusion tube.

T66. The tube according to any of the preceding embodiments, wherein the lumen is configured for guiding at least one of a medical tool and a medical sample.

T67. The tube according to any of the preceding embodiments, wherein the wave-guide(s) are configured for transmitting radiation configured for spectroscopy analysis of the mammal.

T68. The tube according to the preceding embodiment and with the features of T53, wherein the diffusor is configured for scattering the light configured for the spectroscopy analysis, such as infrared light.

T69. The tube according to any of the preceding embodiments, wherein the tube comprises a sensor.

T70. The tube according to any of the preceding embodiments and with the features of T14, wherein the sensor is located at or next to the distal end of the tube.

T71. The tube according to any of the preceding embodiments and with the features of T69, wherein the sensor comprises at least one of
a camera,
a temperature-sensing unit,
a pH value-sensing unit,
a pulse rate-sensing unit,
a pressure-sensing unit,
a blood sugar-sensing unit, and
a sensing unit configured for blood gas-analysis.

T72. The tube according to any of the preceding embodiments, wherein the tube comprises a tube-connector.

T73. The tube according to the preceding embodiment, wherein the tube-connector is configured to connect the wave-guide(s) to a radiation source.

T74. The tube according to the preceding embodiment, wherein the tube-connector comprises a socket.

T75. The tube according to any of the two preceding embodiments, wherein the tube-connector is configured for receiving an optic fibre cable from the radiation source.

T76. The tube according to any of the preceding embodiments with the features of T73 apart from T74 and T75, wherein the tube-connector comprises a plug.

T77. The tube according to the preceding embodiment, wherein the plug is configured to be inserted into a socket of a light source, and wherein the plug is connected to the wave-guide(s).

T78. The tube according to any of the preceding embodiments with the features of T73_0, wherein the tube-connector is configured for connecting at least one of the at least one lumen with a drain for fluid, such as a collector bag.

T79. The tube according to any of the preceding embodiments with the features of T73_0, wherein the tube-connector is configured for connecting at least one of the at least one lumen with a source of fluid.

T80. The tube according to any of the preceding embodiments with the features of T73_0 and T69, wherein the tube is configured for transmitting a read-out of the sensor to the connector.

System Embodiments

Below, embodiments of a system will be discussed. The system embodiments are abbreviated by the letter "5" followed by a number. Whenever reference is herein made to the "system embodiments", these embodiments are meant.

S1. A system, comprising the tube according to any of the tube embodiments, and further comprising a radiation source configured for emitting electro-magnetic radiation.

S2. The system according to the preceding embodiment, wherein the electro-magnetic radiation emitted by the radiation source comprises UV-light.

S3. The system according to the preceding embodiment, wherein the UV-light is UV-C light.

S4. The system according to any of the preceding system embodiments, wherein the electro-magnetic radiation emitted by the radiation source comprises electro-magnetic radiation comprising a wavelength of 222 nm.

S5. The system according to any of the preceding system embodiments, wherein at least 50%, preferably at least 80%, still more preferably 90% and most preferably at least 95 of the electro-magnetic radiation comprise a wavelength of 222+−5 nm.

S6. The system according to the preceding embodiment, wherein at least 50%, preferably at least 80%, still more preferably 90% and most preferably at least 95% of the electro-magnetic radiation comprise a wavelength of substantially 222 nm.

S7. The system according to any of the preceding embodiments with the features of S2, wherein the radiation source is configured for generating monochromatic light.

S8. The system according to any of the preceding system embodiments with the features of S2, wherein the tube is according to any of the tube embodiments with the features of T8, wherein the system is configured for releasing the electro-magnet radiation substantially evenly over a length of the tube.

S9. The system according to any of the preceding system embodiments with the features of S2, wherein the tube is according to any of the tube embodiments with the features of T8, wherein the system is configured for releasing UV-light from the tube comprising a radiant energy density of 0.1 mJ/cm²-300 mJ/cm².

S10. The system according to the preceding embodiment, wherein the system is configured for releasing UV-light from the tube comprising a radiant energy density of 1 mJ/cm² to 100 mJ/cm².

S11. The system according to the preceding embodiment, wherein the system is configured for releasing UV-light from the tube comprising a radiant energy density of 10 mJ/cm²-20 mJ/cm².

S12. The system according to the preceding embodiment, wherein the system is configured for releasing UV-light from the tube comprising a radiant energy density of around 15 mJ/cm².

S13. The system according to any of the preceding embodiments, wherein the system is configured for releasing UV-light from the tube comprising a radiant power density of less than preferably 0.01 mW/cm².

S14. The system according to any of the preceding system embodiments, wherein the system is configured for intermittingly emitting the electro-magnetic radiation.

S15. The system according to any of the preceding system embodiments with the features of S3, wherein the system is configured for intermittingly emitting the UV-C light.

S16. The system according to any of the preceding system embodiments with the features of S3, wherein the radiation source comprises at least one of a UV-C light emitting diode, a laser and a filtered excimer lamp configured for generating the UV-C light.

S17. The system according to any of the preceding system embodiments, wherein the electro-magnetic radiation emitted by the radiation source comprises visible light.

S18. The system according to the preceding embodiment, wherein at least a portion of the wall of the tube is configured for emitting the visible light.

S19. The system according to any of the preceding system embodiments with the features of S17, wherein the radiation source comprises a component configured for generating the visible light, such as an LED.

S20. The system according to any of the preceding system embodiments, wherein the tube is according to any of the tube embodiments with the features of T73, wherein the radiation source comprises a source-connector configured to connect the radiation source to the tube-connector.

S21. The system according to the preceding embodiment, wherein the tube is according to any of the tube embodiments with the features of T76, wherein the source-connector comprises a socket for receiving the plug of the tube-connector.

S22. The system according to any of the preceding embodiments with the features of S20, wherein the radiation source is configured to only provide radiation when the tube-connector and the source-connector are in a connected state.

S23. The system according to the preceding embodiment, wherein the system comprises a safety switch configured for preventing the radiation source from providing radiation when the tube-connector and the source-connector are not in a connected state.

S24. The system according to any of the preceding system embodiments with the features of S20, wherein the source-connector comprises a plug configured to be plugged into the socket of the tube-connector.

Method Embodiments

Below, embodiments of a method will be discussed. The method embodiments are abbreviated by the letter "M" followed by a number. Whenever reference is herein made to the "method embodiments", these embodiments are meant.

M1. A method for using the tube according to any of the tube embodiments, comprising applying the tube to the body of a patient.

M2 The method according to any of the preceding method embodiments, wherein the method further comprises connecting the tube to a source of UV-light.

M3. The method according to any of the preceding method embodiments, wherein the method comprises collecting a bodily fluid by means of the tube.

M4. The method according to any of the preceding method embodiments, wherein the method comprises introducing a liquid into a human body by means of the tube.

M5. The method according to any of the preceding method embodiments, wherein the method comprises introducing a surgical instrument into a human body by means of the tube.

M6. A method for using the system according to any of the system embodiments, comprising applying the tube of the system to the body of the patient.

M7. The method according to the preceding embodiment, wherein the method further comprises connecting the tube to the radiation source.

M8. The method according to any of the two preceding method embodiments, wherein the method comprises collecting a bodily fluid by means of the tube of the system.

M9. The method according to any of the three preceding method embodiments, wherein the method comprises introducing a liquid into a human body by means of the tube of the system.

M10. The method according to any of the four preceding method embodiments, wherein the method comprises introducing the surgical instrument into the human body by means of the tube.

M11. The method according to any of the five preceding embodiments, wherein the method further comprises connecting the system to the power source.

Exemplary features of the invention are further detailed in the figures and the below description of the figures.

DETAILED FIGURE DESCRIPTION

For the sake of clarity, some features may only be shown in some figures, and others may be omitted. However, also the omitted features may be present, and the shown and discussed features do not need to be present in all embodiments.

Figure 1:
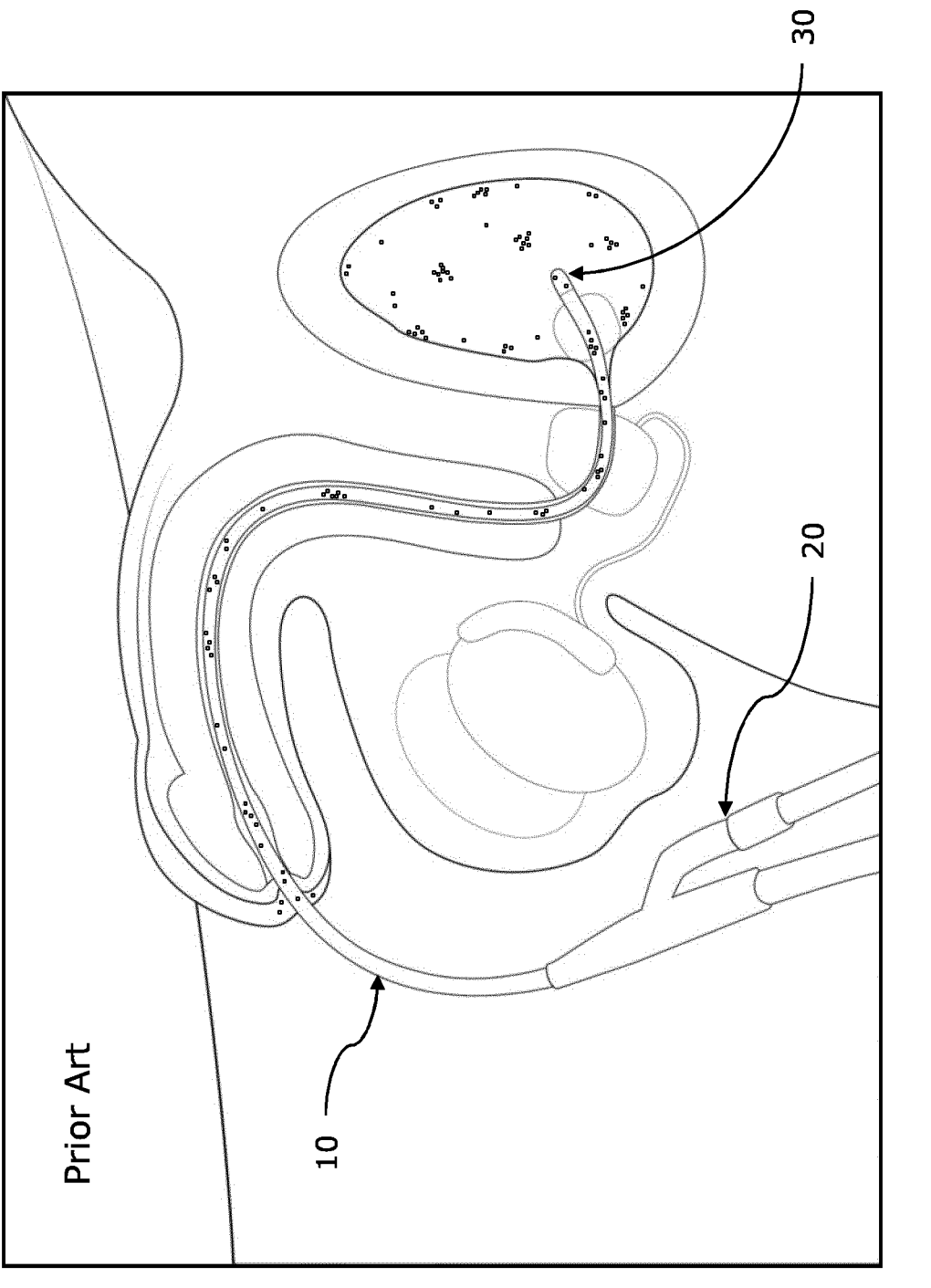
FIG. 1 shows a prior art embodiment of a urinary catheter.

FIG. 1 shows a prior-art embodiment of a urinary catheter. The catheter comprises a tube 10 that is introduced into the human body, e.g. by the urethra. The catheter comprises a distal end 30, which is configured to be introduced into the human body, in this case into the bladder.

The catheter further comprises a proximal end 20, which is opposed to the distal end 30. In other words, the proximal end 20 may not be arranged so as to be introduced into the human body. In use, the proximal end shown in FIG. 1 is connected to a container, such as a collector bag.

In other cases, the catheter may be introduced in other parts of the human body to perform other functions.

Catheters may increase a risk of nosocomial infections. Bacteria and viruses may be propagated by the introduced catheter into a patient's body and result into infections there, such as infections of the urinary tract. Also, introduced urethral catheters normally result in a bacterial population, which is however only treated when complications occur.

Figure 2:
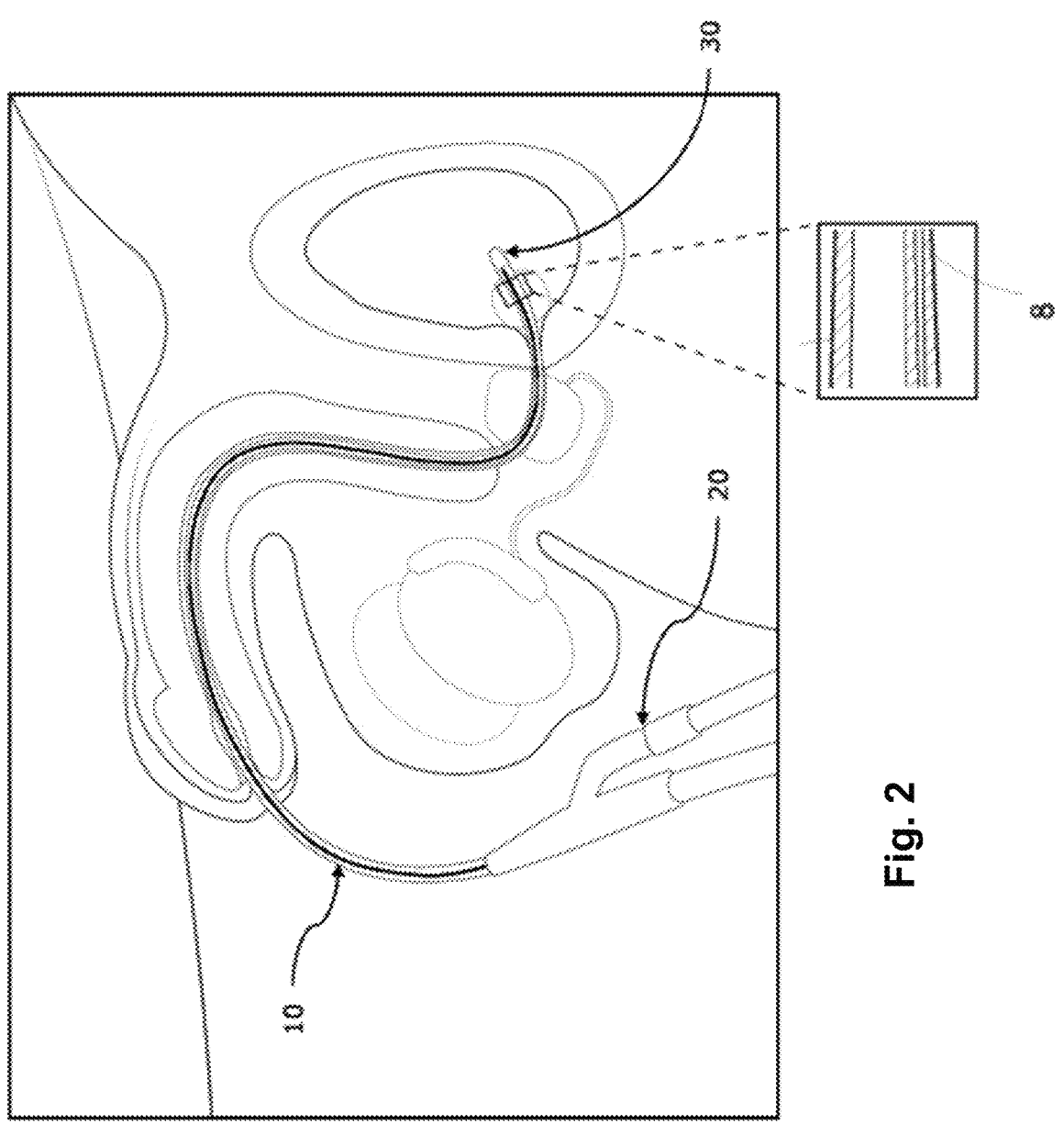
FIG. 2 shows an embodiment of the invention.

FIG. 2 shows an embodiment of the invention. In the shown embodiment, the catheter comprises a wave-guide 8 which transmits electro-magnetic waves, e.g. UV-light. The wave-guide 8 then causes the waves to be transmitted to at least one of an outer surface of the catheter and the distal end 30 of the catheter. The electro-magnetic radiation may then irradiate present bacteria and/or viruses that may cause an infection. Said viruses and/or bacteria may thus be inactivated. The electro-magnetic radiation may particularly be UV-radiation.

In FIG. 2, the UV-radiation comprises a wavelength of 222 nm. A wavelength of 222 nm may be optionally advantageous as discussed by Buonanno et al. and Welch et al. (see above). In particular, such UV-radiation may be suitable for disinfection, without considerably harming the human skin adjacent to the catheter.

Figure 3:
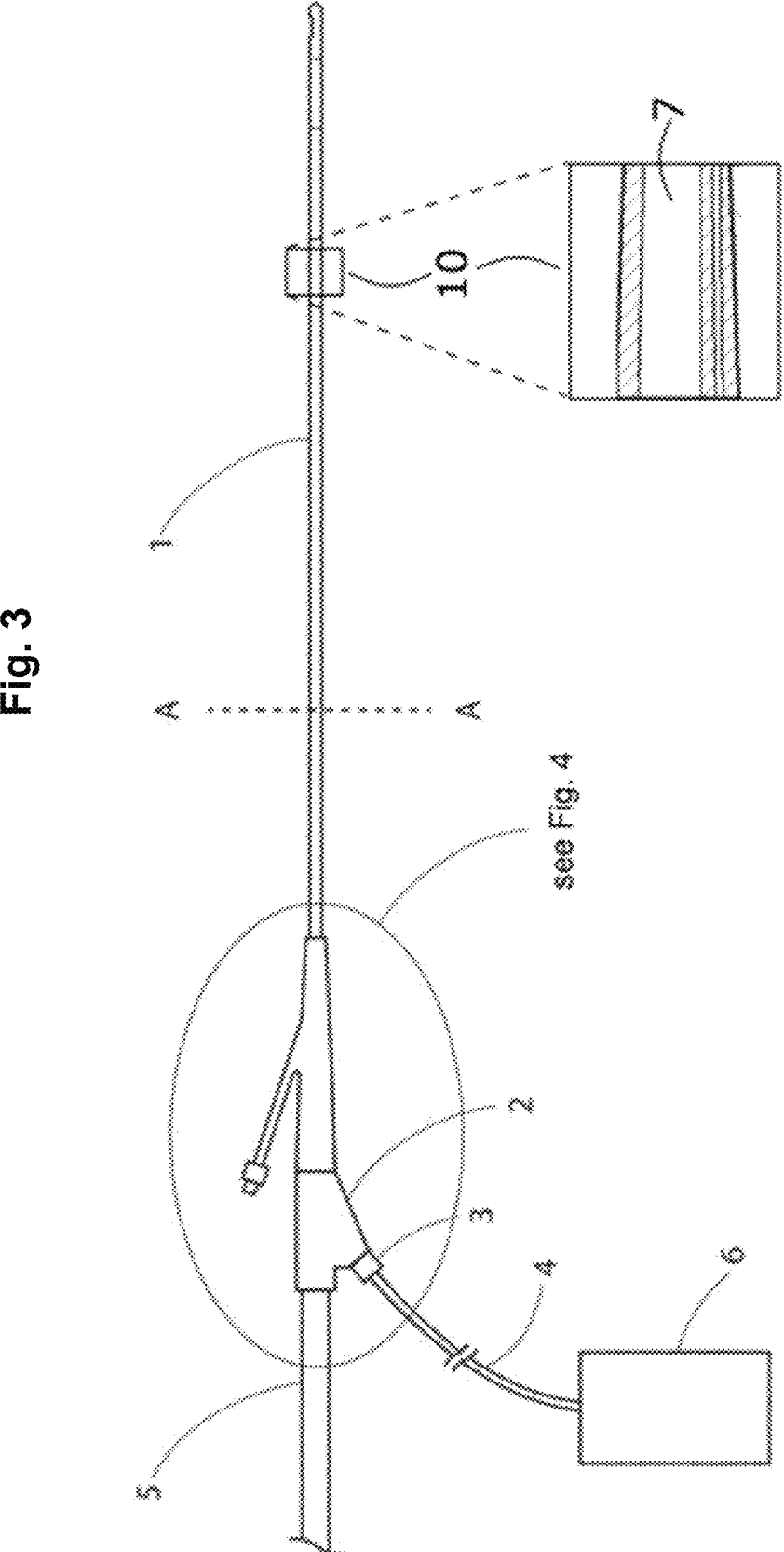
FIG. 3 shows a portion of a catheter.

FIG. 3 shows a catheter. The catheter comprises the tube 10. The tube 10 comprises a wall 1 enclosing at least one lumen 7 which is configured to conduct a fluid, such as a bodily fluid or a fluid to be introduced into the human body.

The tube 10 comprises a tube connector 2 which is configured for connecting the tube to at least one of a radiation source 6 and an intake 5 of a liquid container, such as a collector bag, or an outlet 5 of a fluid source.

Figure 4:
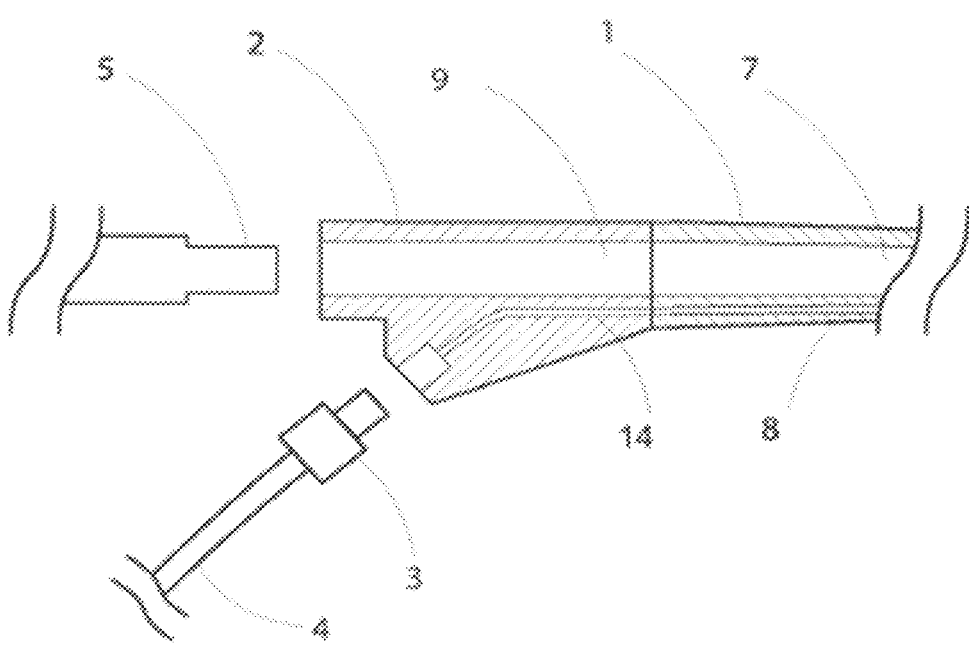
FIG. 4 shows details of a connector.

FIG. 4 shows a detail of the catheter of FIG. 3. The catheter comprises a tube-connector 2. The tube-connector comprises a portion 9 of the lumen 7. Also, the wall 1 enclosing the lumen 7 can be seen. Further, the wave-guide 8 can be seen, as well as a portion of the wave-guide that the tube-connector comprises. The tube-connector 2 may be a part of the tube 10, or the tube connector may be releasable from the tube 10.

Further, a source-connector 3 configured for connecting the tube 10 to the radiation source 6 is shown in FIG. 4. In the example of FIG. 4, the source-connector 3 comprises a wave-guide transmitting electro-magnetic radiation from the source to the tube 10.

The tube-connector 2 comprises a portion 14 of the wave-guide 8 of the tube 10. Further, the intake of the fluid container/outlet of the fluid source 5 is shown.

Figure 5:
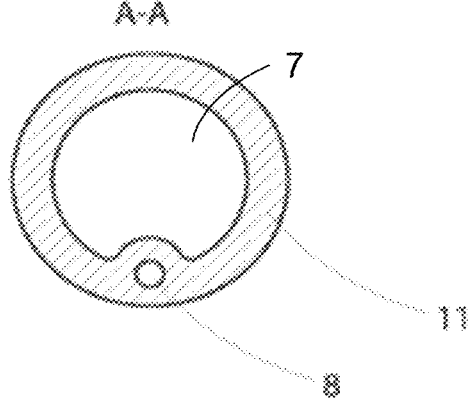
FIG. 5 shows a cross-section of an embodiment of a medical tube.

FIG. 5 shows an exemplary cross-section A-A of the tube 10, as indicated in FIG. 3. In the cross-section, the wall 11 and the wave-guide 8 can be seen. Even though FIG. 5 only shows one wave-guide 8, there may be a plurality of wave-guides 8 in parallel or one after another. As can be seen, the wall 11 encloses the at least one lumen 7.

The wall may be configured for transmitting the electromagnetic radiation, particularly the UV-light. The wall may comprise a polymer configured for transmitting UV-radiation, such as FEP.

The wave-guide 8 may be configured for laterally emitting the electro-magnetic radiation. In other words, the wave-guide may be side-emitting. The wave-guide or wave-guides 8 may each comprise an optic fibre.

The side-emitting feature of the wave-guides may be achieved by means of scattering centers, or by removing a cladding of the optic fibres.

Thus, optionally advantageously, the electro-magnetic radiation may be transmitted to the outer surface of the tube 10 and/or into the lumen 7 of the tube 10.

Figure 6:
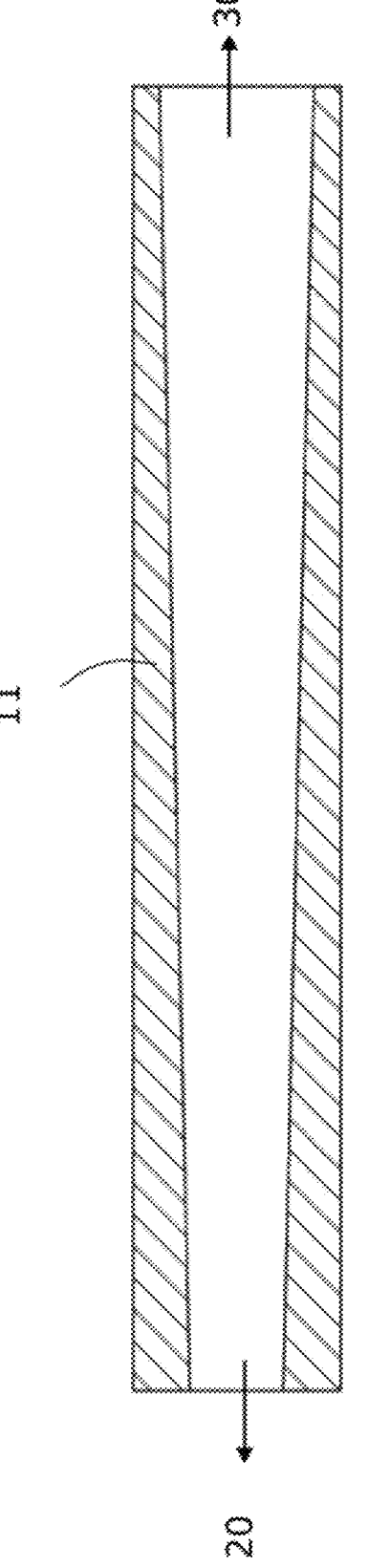
FIG. 6 shows another cross-section of an embodiment of the medical tube.

FIG. 6 shows a cross-section of a portion of the medical tube in an embodiment where a cross-section of the wall 11 of the medical tube comprises a negative gradient from proximal 20 to the distal end 30. This may be optionally advantageous, as thus, the decreasing intensity along the length of the tube may be compensated and a more homogenous irradiation of the inside as well as the outside of the catheter may optionally be achieved.

While in the above, a preferred embodiment has been described with reference to the accompanying drawings, the skilled person will understand that this embodiment was provided for illustrative purpose only and should by no means be construed to limit the scope of the present invention, which is defined by the claims.

Whenever a relative term, such as "about", "substantially" or "approximately" is used in this specification, such a term should also be construed to also include the exact term. That is, e.g., "substantially straight" should be construed to also include "(exactly) straight".

Whenever steps were recited in the above or also in the appended claims, it should be noted that the order in which the steps are recited in this text may be accidental. That is, unless otherwise specified or unless clear to the skilled person, the order in which steps are recited may be accidental. That is, when the present document states, e.g., that a method comprises steps (A) and (B), this does not necessarily mean that step (A) precedes step (B), but it is also possible that step (A) is performed (at least partly) simultaneously with step (B) or that step (B) precedes step (A). Furthermore, when a step (X) is said to precede another step (Z), this does not imply that there is no step between steps (X) and (Z). That is, step (X) preceding step (Z) encompasses the situation that step (X) is performed directly before step (Z), but also the situation that (X) is performed before one or more steps (Y1), . . . , followed by step (Z). Corresponding considerations apply when terms like "after" or "before" are used.

NUMBERED REFERENCE SIGNS

1 Wall
2 Tube-connector
3 Source-connector
4 Wave-guide of the source
5 Connection to container
6 Radiation source
7 Lumen
8 Wave-guide of the tube
9 Lumen of the tube-connector
10 Tube
11 Wall
14 Wave-guide of the tube-connector
20 Proximal end
30 Distal end

The invention claimed is:

1. A tube comprising at least one lumen, and a wall comprising at least one or a plurality of wave-guide(s) and enclosing the at least one lumen, wherein the tube comprises a distal end configured for being introduced into a body of a mammal and a proximal end comprising a tube-connector, wherein the wave-guide(s) are configured to conduct electro-magnetic radiation along the tube, wherein the tube is configured to emit at least a part of the radiation into the lumen and/or to an outer surface of the tube, wherein the wave-guide(s) are configured for transmitting and side-emitting UV-light comprising a wave-length of 200-280 nm, wherein the wall comprises fluorinated ethylene-propylene, and wherein the wall of the tube comprises a cross-section area, and wherein the cross-section area of the wall of the tube comprises a negative gradient along the tube from the proximal to the distal end.

2. The tube according to claim 1, wherein the wave-guide(s) are permanently attached to at least a portion of the wall, and wherein each of the wave-guide(s) comprises an optic fibre.

3. The tube according to claim 2, wherein the optic fibre comprises a high-OH silica core.

4. The tube according to claim 1, wherein the wave-guide(s) comprise a liquid light guide, wherein the liquid light guide comprises a canal for a light guide liquid, wherein the canal comprises the light guide liquid.

5. The tube according to claim 1, wherein the wave-guide(s) comprise a gradient of a side-emittance of the UV-light, and wherein the side-emittance of the UV-light increases from the proximal to the distal end.

6. The tube according to claim 1, wherein the tube comprises a spherical diffusor at the distal end.

7. The tube according to claim 1, wherein the tube comprises a fluorescent element.

8. The tube according to claim 1, wherein the tube is at least one of a catheter, a drain and an infusion tube.

9. The tube according to claim 1, wherein the tube-connector is configured to connect the wave-guide(s) to a radiation source.

10. The tube according to claim 1, wherein the wave-guide(s) are configured for transmitting and side-emitting the UV-light comprising a wave-length of 210-260 nm.

11. The tube according to claim 1, wherein the wave-guide(s) are configured for transmitting and side-emitting the UV-light comprising a wave-length of 210-230 nm.

12. A system, comprising the tube according to claim 1, and further comprising a radiation source configured for emitting the electro-magnetic radiation, wherein the electro-magnetic radiation comprises UV-C light.

13. The system according to claim 12, wherein at least 50% of the electro-magnetic radiation comprise a wave-length of 222±5 nm.

14. The system according to claim 12, wherein the system is configured for releasing the electro-magnetic radiation substantially evenly over a length of the tube and wherein the system is configured for intermittingly emitting the UV-C light.

15. The system according to claim 12, wherein the tube-connector comprises a socket, and wherein the radiation source comprises a source-connector configured to connect the radiation source to the tube-connector, wherein the source-connector comprises a plug configured to be plugged into the socket of the tube-connector.

16. The system according to claim 12, wherein at least 80% of the electro-magnetic radiation comprises a wave-length of 222±5 nm.

17. The system according to claim 12, wherein at least 95% of the electro-magnetic radiation comprises a wave-length of 222±5 nm.

18. A method for using the tube according to claim 1, comprising applying the tube to a body of a patient.

19. A method for using the system according to claim 12, comprising applying the tube of the system to a body of a patient.

* * * * *